US00PP17103P2

(12) United States Plant Patent
Morgan

(10) Patent No.: US PP17,103 P2
(45) Date of Patent: Sep. 19, 2006

(54) ***ARGYRANTHEMUM* PLANT NAMED 'COBWHITE'**

(50) Latin Name: *Argyranthemum frutescens*
Varietal Denomination: Cobwhite

(75) Inventor: Mal Morgan, Macquarie Fields (AU)

(73) Assignee: Nuflora International Pty. Ltd., Macquarie Fields (AU)

( * ) Notice: Subject to any disclaimer, the term of this patent is extended or adjusted under 35 U.S.C. 154(b) by 328 days.

(21) Appl. No.: 10/959,767

(22) Filed: Oct. 6, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—C. A. Whealy

(57) ABSTRACT

A new and distinct cultivar of *Argyranthemum* plant named 'Cobwhite', characterized by its compact, upright and mounded plant habit; freely branching habit, dense and bushy plants; freely flowering habit with numerous inflorescences per plant; daisy-type inflorescence form with white-colored ray florets and yellow orange-colored disc florets.

1 Drawing Sheet

Botanical classification/cultivar denomination: *Argyranthemum frutescens* cultivar Cobwhite.

BACKGROUND OF THE INVENTION

The present invention relates to a new and distinct cultivar of *Argyranthemum* plant, botanically known as *Argyranthemum frutescens* and hereinafter referred to by the cultivar name 'Cobwhite'.

The new *Argyranthemum* is a whole plant mutation of the *Argyranthemum* cultivar Cobsing, disclosed in U.S. Plant Pat. No. 13,541. The new Poinsettia was discovered and selected by the Inventor in a controlled environment in Encinitas, Calif. on May 30, 2002. The new *Argyranthemum* was selected on the basis its unique ray floret coloration.

Asexual reproduction of the new *Argyranthemum* by terminal cuttings in a controlled environment in Encinitas, Calif. since Jun. 12, 2002, has shown that the unique features of this new *Argyranthemum* are stable and reproduced true to type in successive generations.

SUMMARY OF THE INVENTION

The new *Argyranthemum* has not been observed under all possible environmental conditions. The phenotype may vary somewhat with variations in environment such as temperature and light intensity without, however, any variance in genotype.

The following characteristics have been repeatedly observed and are determined to be basic characteristics of 'Cobwhite' and distinguish the new *Argyranthemum* as a new and distinct cultivar:

1. Compact, upright and mounded plant habit.
2. Freely branching habit, dense and bushy plants.
3. Freely flowering habit with numerous inflorescences per plant.
4. Daisy-type inflorescence form with white-colored ray florets and yellow orange-colored disc florets.

Plants of the new *Argyranthemum* differ from plants of the cultivar Cobsing primarily in ray floret coloration as plants of the cultivar Cobsing have pink-colored ray florets.

Plants of the new *Argyranthemum* can be compared to plants of the cultivar Summer Ice, not patented. In side-by-side comparisons conducted in Encinitas, Calif., plants of the new *Argyranthemum* differed primarily from plants of the cultivar Summer Ice in the following characteristics:

1. Plants of the new *Argyranthemum* were more compact than plants of the cultivar Summer Ice.
2. Plants of the new *Argyranthemum* and the cultivar Summer Ice differed in foliage coloration as plants of the cultivar Summer Ice had silvery green-colored foliage.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Argyranthemum*.

The photograph at the top of the sheet comprises a side perspective view of typical flowering plants of 'Cobwhite' grown in a container.

The photograph at the bottom of the sheet comprises a close-up view of typical inflorescences of 'Cobwhite'.

DETAILED BOTANICAL DESCRIPTION

The aforementioned photographs, following observations and averaged measurements describe plants grown in Encinitas, Calif., in an outdoor nursery under full sunlight during the winter and spring with day temperatures ranging from 15 to 24° C. and night temperatures ranging from 10 to 19° C. Plants were grown in one-gallon containers with two plants per container. Plants were pinched one time about five weeks after planting. Plants had been growing for about 16 weeks when the photographs and description were taken. Color references are made to The Royal Horticultural Society Colour Chart, 1995 Edition, except where general terms of ordinary dictionary significance are used.

Botanical classification: *Argyranthemum frutescens* cultivar Cobwhite.

Parentage: Whole plant mutation of the *Argyranthemum* cultivar Cobsing, disclosed in U.S. Plant Pat. No. 13,541.

Propagation:

*Type.*—Terminal vegetative cuttings.

*Time to initiate roots.*—About 10 days at 20° C.

*Time to produce a rooted cutting.*—About three weeks at 20° C.

*Root description.*—Fibrous, fine; white in color.

*Rooting description.*—Freely branching; dense.

Plant description:

*General appearance.*—Inverted triangle; compact, upright and mounded plant form with dense foliage and inflorescences held above and beyond the foliage. Vigorous growth habit.

*Plant height.*—About 40 cm.

*Plant width, single plant.*—About 45 cm.

*Lateral branch description.*—Quantity per plant: About two or three primary lateral branches each with about 12 to 14 secondary lateral branches. Length, primary laterals: About 40 cm. Length, secondary laterals: About 31 cm. Diameter, primary laterals: About 1 cm. Diameter, secondary laterals: About 4 mm. Internode length: About 1 to 1.5 cm. Aspect: Upright to outwardly spreading. Texture: Smooth, glabrous. Color: 146C.

*Foliage description.*—Arrangement: Alternate, simple. Length: About 4.5 cm. Width: About 5 cm. Shape: Pinnatifid, deeply and finely dissected. Apex: Acute. Base: Attenuate. Margin: Entire; deeply and finely dissected; sinuses parallel. Texture, upper and lower surfaces: Smooth, glabrous. Venation pattern: Pinnate. Petiole length: About 2.5 cm. Petiole diameter: About 2.5 mm. Petiole texture, upper and lower surfaces: Smooth, glabrous. Color: Developing foliage, upper surface: 147A. Developing foliage, lower surface: 147B. Fully expanded foliage, upper surface: 146A. Fully expanded foliage, lower surface: 146B. Venation, upper and lower surfaces: 146B. Petiole, upper surface: 146C. Petiole, lower surface: 147B.

Inflorescence description:

*Appearance.*—Daisy-type inflorescence form with ligulate ray florets. Disc and ray florets develop acropetally on a capitulum. Inflorescences held upright and outwardly on terminal and axillary peduncles. Inflorescences positioned perpendicular to the peduncles. Inflorescences persistent.

*Flowering response.*—Under natural conditions, plant flower from spring to early fall in Southern California; plants flower continuous during this period.

*Inflorescence longevity.*—Inflorescences last about ten days on the plant.

*Quantity of inflorescences.*—Freely flowering, about 30 inflorescences develop per lateral branch.

*Fragrance.*—Sour, unpleasant.

*Inflorescence size.*—Diameter: About 4 cm. Depth (height): About 1.2 cm. Diameter of disc: About 1.1 cm. Receptacle height: About 6 mm. Receptacle diameter: About 1.2 cm.

*Inflorescence buds, at stage of showing color.*—Height: About 1.1 cm. Diameter: About 9 mm. Shape: Ovoid. Color: 155B.

*Ray florets.*—Quantity per inflorescence: About 20 arranged in a single whorl. Shape: Ligulate. Length: About 2 cm. Width: About 7 mm. Apex: Emarginate. Base: Acute. Margin: Entire. Texture, upper and lower surfaces: Smooth, satiny. Aspect: Initially upright; when mature, slightly cupped upright to horizontal. Color: When opening, upper surface: 155A. When opening, lower surface: 155D. Fully opened, upper surface: 155B. Fully opened, lower surface: More white than 155D.

*Disc florets.*—Arrangement: Massed at the center of the inflorescence. Quantity per inflorescence: About 200. Shape: Tubular, elongated; apex, five-pointed; base, fused. Length: About 5 mm. Diameter, apex: About 1.5 mm. Diameter, base: Less than 1 mm. Color: Apex: 14A. Mid-section and base: 1C.

*Involucral bracts* (*phyllaries*).—Appearance: Scale-like; margins, papery. Quantity per inflorescence: About 20. Length: About 2 mm. Width: About 1.5 mm. Shape: Elliptic. Apex: Acute. Base: Truncate. Margin: Entire. Texture, upper and lower surfaces: Glabrous, smooth. Color, upper surface: 143B. Color, lower surface: 143A.

*Peduncle.*—Strength: Moderately strong; wiry. Aspect: Upright to about 45° from vertical. Length, terminal inflorescence: About 5.5 cm. Length, fourth inflorescence: About 9.8 cm. Diameter: About 1 mm. Texture: Smooth, glabrous. Color: 146B.

*Reproductive organs.*—Androecium: Present on disc florets only. Quantity per floret: Five. Anther shape: Oblong. Anther length: Less than 1 mm. Anther color: 17A. Amount of pollen: Scarce. Pollen color: 17A. Gynoecium: Present on ray and disc florets. Quantity per floret: One. Pistil length: About 4 mm. Stigma shape: Two-parted. Stigma color: 14A. Style length: About 2.5 mm. Style color: 145D. Ovary color: 155A. Seed/fruit: Seed and fruit production has not been observed.

Disease/pest resistance: Resistance to pathogens and pests common to *Argyranthemums* has not been observed on plants grown under commercial conditions.

Temperature/weather tolerance: Plants of the new *Argyranthemum* have been observed to be tolerant to rain, wind and to temperatures from −1 to 30° C.

It is claimed:

1. A new and distinct cultivar of *Argyranthemum* plant named 'Cobwhite', as illustrated and described.

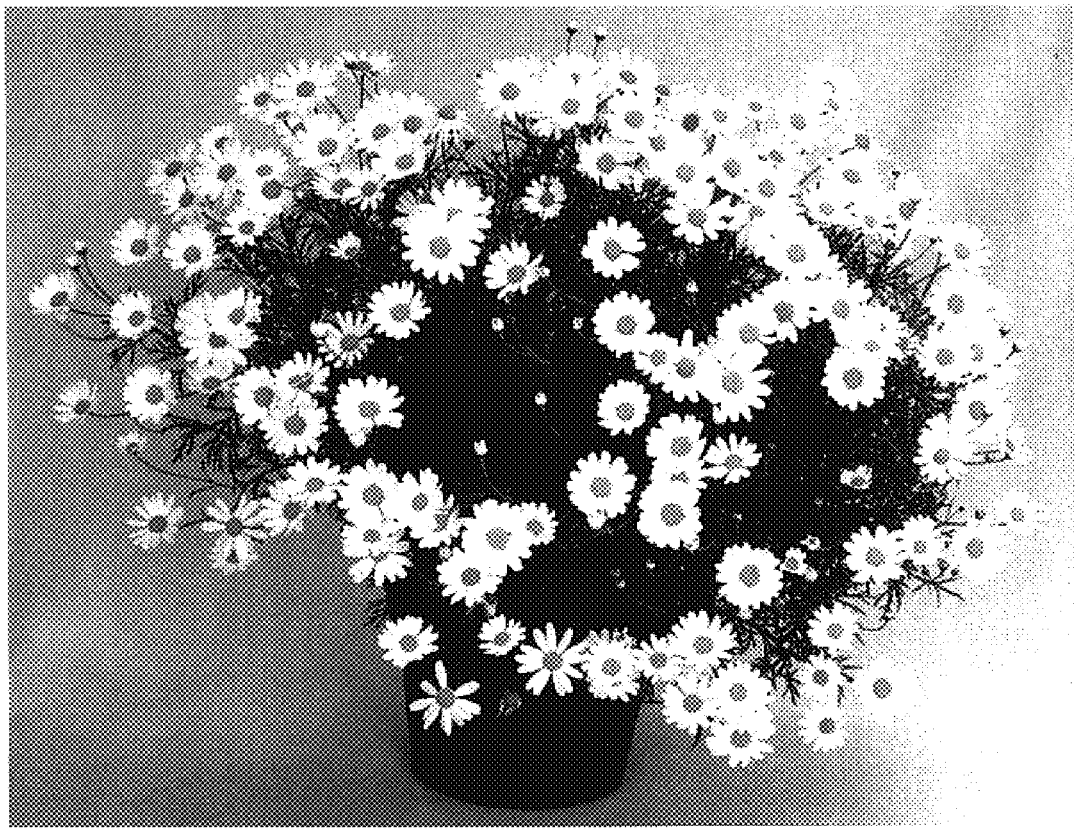
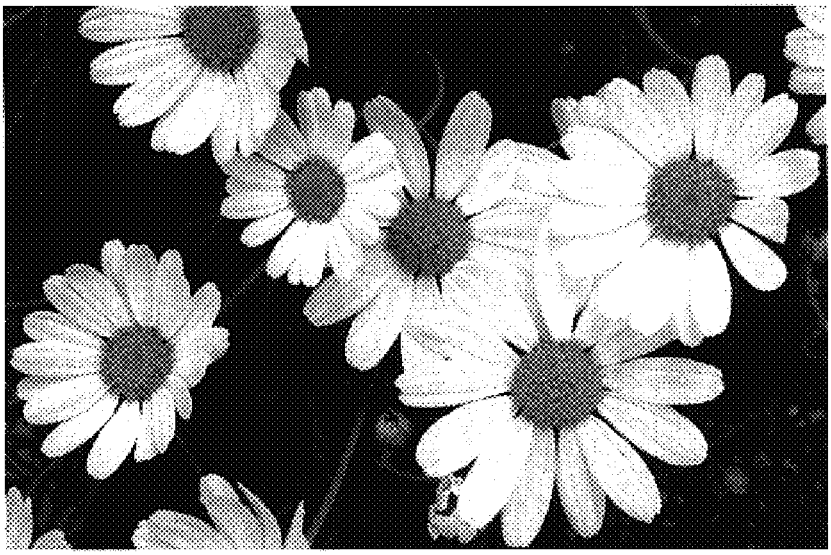

* * * * *